United States Patent [19]

Smith et al.

[11] Patent Number: 5,464,938
[45] Date of Patent: Nov. 7, 1995

[54] ISOLATED VIRAL PROTEIN TNF ANTAGONISTS

[75] Inventors: Craig A. Smith; Raymond G. Goodwin, both of Seattle, Wash.

[73] Assignee: Immunex Corporation, Seattle, Wash.

[21] Appl. No.: 292,549

[22] Filed: Aug. 18, 1994

Related U.S. Application Data

[63] Continuation of Ser. No. 963,330, Oct. 19, 1992, abandoned, which is a continuation-in-part of Ser. No. 507,213, Apr. 9, 1990, abandoned.

[51] Int. Cl.$^6$ .................................................. C07K 14/065
[52] U.S. Cl. ......................... 530/350; 530/351; 530/395
[58] Field of Search ................................. 530/350, 351, 530/375, 392; 435/69.1; 514/2; 536/23.72

[56] References Cited

PUBLICATIONS

Bozan, *Immunology Today* 11(10), 1990, pp. 350–354.
Daspin et al, *Science*, 257, 1992, pp. 369–373.
Casman, *Cytokine* 5(2) 1993, pp. 95–106.
Mallett et al *EMBO J* 1990, pp. 1063–1068.
Patel et al, *J. Gen Virol* 71, 1990, pp. 2013–2021.
Pickup et al, *PNAS*, 79, 1982 pp. 7112–7116.
Parsons et al, *Virology*, 175, 1990, pp. 69–80.
Hu, *Virology* 181, 1991, pp. 716–720.
Gooding et al, *J. Immunol* 145(9) 1990, pp. 3080–3086 (abstract only).
Levi et al, *PNAS* 90(4) 1993, pp. 1541–1545 (abst only).

*Primary Examiner*—Stephen G. Walsh
*Assistant Examiner*—John D. Ulm
*Attorney, Agent, or Firm*—Patricia Anne Perkins

[57] ABSTRACT

Isolated viral proteins, and pharmaceutical compositions made therefrom, are disclosed which are capable of binding to cytokines, thereby functioning as cytokine antagonists. Also disclosed are processes for preparing isolated vital protein cytokine antagonists.

6 Claims, No Drawings

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
    ( A ) LENGTH: 1200 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Rabbit fibroma virus ( v i i ) IMMEDIATE SOURCE:
    ( B ) CLONE: T2 ORF ( i x ) FEATURE:
    ( A ) NAME/KEY: CDS
( B ) LOCATION: 192..1169

( i x ) FEATURE:
( A ) NAME/KEY: mat_peptide
( B ) LOCATION: 192..1166

( x i ) SEQUENCE DESCRIPTION: SEQ ID NO:1:

```
GTGATTGAGT TGTTCATGAG GTTGATCGCG GATTATGAGA TTTCACATAT CAGGTCCGTG        60

ATCAATATTC GTTTACAATG CTTCGCTCCT CGAAAAAGTC GTAACATCTA AATTGGCTCT       120

CTCATTCGGT TATAATTGAT TCCTTCTTTT TCTTGTACAA AAATATAAAA ATAATTACAA       180

CATTATATAT T ATG CTT CGT TTA ATT GCA CTA CTA GTA TGT GTC GTG TAC       230
             Met Leu Arg Leu Ile Ala Leu Leu Val Cys Val Val Tyr
              1               5                  10

GTA TAC GGA GAT GAT GTA CCG TAT TCT TCC AAT CAA GGA AAA TGT GGA        278
Val Tyr Gly Asp Asp Val Pro Tyr Ser Ser Asn Gln Gly Lys Cys Gly
     15                  20                  25

GGA CAC GAC TAC GAA AAA GAC GGA CTG TGT TGT GCA TCC TGT CAT CCA        326
Gly His Asp Tyr Glu Lys Asp Gly Leu Cys Cys Ala Ser Cys His Pro
 30                  35                  40                  45

GGG TTT TAT GCC TCT AGA TTG TGC GGA CCC GGG TCC AAT ACG GTG TGT        374
Gly Phe Tyr Ala Ser Arg Leu Cys Gly Pro Gly Ser Asn Thr Val Cys
                 50                  55                  60

TCT CCG TGT GAA GAC GGA ACC TTT ACG GCG AGT ACT AAC CAT GCC CCT        422
Ser Pro Cys Glu Asp Gly Thr Phe Thr Ala Ser Thr Asn His Ala Pro
             65                  70                  75

GCG TGC GTA AGT TGT CGA GGT CCG TGT ACG GGG CAT CTA TCC GAG TCT        470
Ala Cys Val Ser Cys Arg Gly Pro Cys Thr Gly His Leu Ser Glu Ser
         80                  85                  90

CAA CCG TGC GAT AGA ACC CAC GAT AGA GTC TGC AAT TGT TCT ACG GGG        518
Gln Pro Cys Asp Arg Thr His Asp Arg Val Cys Asn Cys Ser Thr Gly
     95                 100                 105

AAC TAT TGT CTG TTG AAA GGA CAG AAC GGA TGT AGG ATA TGT GCC CCC        566
Asn Tyr Cys Leu Leu Lys Gly Gln Asn Gly Cys Arg Ile Cys Ala Pro
110                 115                 120                 125

CAG ACA AAG TGT CCC GCG GGA TAT GGC GTC TCT GGA CAC ACG CGA GCG        614
Gln Thr Lys Cys Pro Ala Gly Tyr Gly Val Ser Gly His Thr Arg Ala
                130                 135                 140

GGA GAT ACT CTC TGT GAG AAA TGT CCT CCG CAT ACG TAT TCC GAT TCT        662
Gly Asp Thr Leu Cys Glu Lys Cys Pro Pro His Thr Tyr Ser Asp Ser
            145                 150                 155

CTG TCT CCA ACA GAG AGA TGC GGT ACA TCG TTT AAT TAC ATC AGT GTG        710
Leu Ser Pro Thr Glu Arg Cys Gly Thr Ser Phe Asn Tyr Ile Ser Val
        160                 165                 170

GGA TTC AAT CTA TAT CCC GTA AAC GAA ACG TCT TGT ACG ACG ACC GCT        758
```

```
Gly Phe Asn Leu Tyr Pro Val Asn Glu Thr Ser Cys Thr Thr Thr Ala
    175                 180                 185

GGA CAC AAC GAA GTG ATC AAA ACG AAG GAG TTT ACA GTT ACG TTA AAT        806
Gly His Asn Glu Val Ile Lys Thr Lys Glu Phe Thr Val Thr Leu Asn
190                 195                 200                 205

TAC ACG GAT TGT GAT CCT GTC TTT CAC ACG GAA TAC TAC GCA ACG AGT        854
Tyr Thr Asp Cys Asp Pro Val Phe His Thr Glu Tyr Tyr Ala Thr Ser
                210                 215                 220

GGA AAA GAA GGA GCT GGT GGA TTC TTC ACG GGA ACA GAT ATA TAC CAG        902
Gly Lys Glu Gly Ala Gly Gly Phe Phe Thr Gly Thr Asp Ile Tyr Gln
            225                 230                 235

AAC ACC ACC AAG GTG TGT ACA CTC AAC GTG GAG ATC CAG TGT TCT GAG        950
Asn Thr Thr Lys Val Cys Thr Leu Asn Val Glu Ile Gln Cys Ser Glu
        240                 245                 250

GGA GAC GAT ATA CAT ACA TTG CAG AAG ACG AAC GGG GGG TCT ACC ATG        998
Gly Asp Asp Ile His Thr Leu Gln Lys Thr Asn Gly Gly Ser Thr Met
    255                 260                 265

CCT CAT TCG GAG ACG ATT ACC GTC GTA GGA AGT TGT CTG TCC GAC GTT       1046
Pro His Ser Glu Thr Ile Thr Val Val Gly Ser Cys Leu Ser Asp Val
270                 275                 280                 285

AAT GTA GAT ATC ATG TAC AGC GAC ACC AAC CAC CCC GGG GAG GTC GAT       1094
Asn Val Asp Ile Met Tyr Ser Asp Thr Asn His Pro Gly Glu Val Asp
                290                 295                 300

GAC TTC GTG GAA TAT CAT TGG GGG ACG CGT CTC CGT TTC TTT CCC TTA       1142
Asp Phe Val Glu Tyr His Trp Gly Thr Arg Leu Arg Phe Phe Pro Leu
            305                 310                 315

CCC AAA CGA TGT ACC CCA GTC TCG TAGGGTTTTT CTTTCTCGTT AATTTCTTAA       1196
Pro Lys Arg Cys Thr Pro Val Ser
        320                 325

AAAA                                                                   1200
```

( 2 ) INFORMATION FOR SEQ ID NO:2:

( i ) SEQUENCE CHARACTERISTICS:
        ( A ) LENGTH: 325 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Leu Arg Leu Ile Ala Leu Leu Val Cys Val Val Tyr Val Tyr Gly
1               5                   10                  15

Asp Asp Val Pro Tyr Ser Ser Asn Gln Gly Lys Cys Gly Gly His Asp
            20                  25                  30

Tyr Glu Lys Asp Gly Leu Cys Cys Ala Ser Cys His Pro Gly Phe Tyr
        35                  40                  45

Ala Ser Arg Leu Cys Gly Pro Gly Ser Asn Thr Val Cys Ser Pro Cys
    50                  55                  60

Glu Asp Gly Thr Phe Thr Ala Ser Thr Asn His Ala Pro Ala Cys Val
65                  70                  75                  80

Ser Cys Arg Gly Pro Cys Thr Gly His Leu Ser Glu Ser Gln Pro Cys
            85                  90                  95

Asp Arg Thr His Asp Arg Val Cys Asn Cys Ser Thr Gly Asn Tyr Cys
            100                 105                 110

Leu Leu Lys Gly Gln Asn Gly Cys Arg Ile Cys Ala Pro Gln Thr Lys
        115                 120                 125

Cys Pro Ala Gly Tyr Gly Val Ser Gly His Thr Arg Ala Gly Asp Thr
130                 135                 140
```

| Leu | Cys | Glu | Lys | Cys | Pro | Pro | His | Thr | Tyr | Ser | Asp | Ser | Leu | Ser | Pro |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Thr | Glu | Arg | Cys | Gly | Thr | Ser | Phe | Asn | Tyr | Ile | Ser | Val | Gly | Phe | Asn |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Leu | Tyr | Pro | Val | Asn | Glu | Thr | Ser | Cys | Thr | Thr | Ala | Gly | His | Asn |
|-----|-----|-----|-----|-----|-----|-----|-----|-----|-----|-----|-----|-----|-----|-----|
|     |     |     | 180 |     |     |     |     | 185 |     |     |     | 190 |     |     |

| Glu | Val | Ile | Lys | Thr | Lys | Glu | Phe | Thr | Val | Thr | Leu | Asn | Tyr | Thr | Asp |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Cys | Asp | Pro | Val | Phe | His | Thr | Glu | Tyr | Tyr | Ala | Thr | Ser | Gly | Lys | Glu |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Gly | Ala | Gly | Gly | Phe | Phe | Thr | Gly | Thr | Asp | Ile | Tyr | Gln | Asn | Thr | Thr |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Lys | Val | Cys | Thr | Leu | Asn | Val | Glu | Ile | Gln | Cys | Ser | Glu | Gly | Asp | Asp |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Ile | His | Thr | Leu | Gln | Lys | Thr | Asn | Gly | Gly | Ser | Thr | Met | Pro | His | Ser |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Glu | Thr | Ile | Thr | Val | Val | Gly | Ser | Cys | Leu | Ser | Asp | Val | Asn | Val | Asp |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Ile | Met | Tyr | Ser | Asp | Thr | Asn | His | Pro | Gly | Glu | Val | Asp | Asp | Phe | Val |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Glu | Tyr | His | Trp | Gly | Thr | Arg | Leu | Arg | Phe | Phe | Pro | Leu | Pro | Lys | Arg |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Cys | Thr | Pro | Val | Ser |
|-----|-----|-----|-----|-----|
|     |     |     |     | 325 |

( 2 ) INFORMATION FOR SEQ ID NO:3:

( i ) SEQUENCE CHARACTERISTICS:
           ( A ) LENGTH: 1064 base pairs
           ( B ) TYPE: nucleic acid
           ( C ) STRANDEDNESS: double
           ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
           ( A ) ORGANISM: Myxoma virus ( v i i i ) IMMEDIATE SOURCE:
           ( B ) CLONE: T2 ORF ( i x ) FEATURE:
           ( A ) NAME/KEY: mat_peptide
           ( B ) LOCATION: 2..979

( i x ) FEATURE:
           ( A ) NAME/KEY: CDS
           ( B ) LOCATION: 2..982

( x i ) SEQUENCE DESCRIPTION: SEQ ID NO:3:

| C | ATG | TTT | CGT | TTA | ACG | CTA | CTA | CTC | GCG | TAC | GTC | GCG | TGC | GTA | TAC |    | 46 |
|---|-----|-----|-----|-----|-----|-----|-----|-----|-----|-----|-----|-----|-----|-----|-----|----|----|
|   | Met | Phe | Arg | Leu | Thr | Leu | Leu | Leu | Ala | Tyr | Val | Ala | Cys | Val | Tyr |    |    |
|   | 1   |     |     |     | 5   |     |     |     |     | 10  |     |     |     |     | 15  |    |    |

| GGG | GGC | GGT | GCC | CCG | TAT | GGC | GCG | GAT | CGA | GGA | AAA | TGT | AGA | GGG | AAC | 94 |
|-----|-----|-----|-----|-----|-----|-----|-----|-----|-----|-----|-----|-----|-----|-----|-----|----|
| Gly | Gly | Gly | Ala | Pro | Tyr | Gly | Ala | Asp | Arg | Gly | Lys | Cys | Arg | Gly | Asn |    |
|     |     |     |     | 20  |     |     |     |     | 25  |     |     |     |     | 30  |     |    |

| GAC | TAC | GAA | AAG | GAC | GGA | CTG | TGT | TGT | ACC | TCC | TGT | CCT | CCC | GGG | TCG | 142 |
|-----|-----|-----|-----|-----|-----|-----|-----|-----|-----|-----|-----|-----|-----|-----|-----|-----|
| Asp | Tyr | Glu | Lys | Asp | Gly | Leu | Cys | Cys | Thr | Ser | Cys | Pro | Pro | Gly | Ser |     |
|     |     |     | 35  |     |     |     |     | 40  |     |     |     |     | 45  |     |     |     |

| | | | | | | | | | | | | | | | | |
|---|---|---|---|---|---|---|---|---|---|---|---|---|---|---|---|---|
| TAC | GCC | TCT | AGG | TTA | TGC | GGA | CCC | GGG | TCC | GAC | ACG | GTA | TGT | TCT | CCG | 190 |
| Tyr | Ala | Ser | Arg | Leu | Cys | Gly | Pro | Gly | Ser | Asp | Thr | Val | Cys | Ser | Pro | |
| | | 50 | | | | | 55 | | | | | 60 | | | | |
| TGC | AAG | AAC | GAA | ACC | TTT | ACG | GCG | AGT | ACG | AAC | CAC | GCT | CCC | GCG | TGC | 238 |
| Cys | Lys | Asn | Glu | Thr | Phe | Thr | Ala | Ser | Thr | Asn | His | Ala | Pro | Ala | Cys | |
| | 65 | | | | | 70 | | | | | 75 | | | | | |
| GTA | AGT | TGT | CGA | GGG | CGG | TGC | ACA | GGC | CAC | CTA | TCC | GAG | TCT | CAA | TCG | 286 |
| Val | Ser | Cys | Arg | Gly | Arg | Cys | Thr | Gly | His | Leu | Ser | Glu | Ser | Gln | Ser | |
| 80 | | | | | 85 | | | | | 90 | | | | | 95 | |
| TGT | GAT | AAA | ACC | CGC | GAT | AGA | GTC | TGC | GAC | TGT | TCT | GCG | GGG | AAC | TAT | 334 |
| Cys | Asp | Lys | Thr | Arg | Asp | Arg | Val | Cys | Asp | Cys | Ser | Ala | Gly | Asn | Tyr | |
| | | | 100 | | | | | 105 | | | | | 110 | | | |
| TGT | CTG | TTG | AAA | GGA | CAG | GAG | GGG | TGT | AGG | ATA | TGC | GCT | CCC | AAA | ACG | 382 |
| Cys | Leu | Leu | Lys | Gly | Gln | Glu | Gly | Cys | Arg | Ile | Cys | Ala | Pro | Lys | Thr | |
| | | | 115 | | | | | 120 | | | | | 125 | | | |
| AAG | TGT | CCC | GCG | GGG | TAT | GGC | GTC | TCC | GGA | CAT | ACG | CGT | ACG | GGC | GAC | 430 |
| Lys | Cys | Pro | Ala | Gly | Tyr | Gly | Val | Ser | Gly | His | Thr | Arg | Thr | Gly | Asp | |
| | | 130 | | | | | 135 | | | | | 140 | | | | |
| GTG | CTC | TGC | ACA | AAA | TGT | CCT | CGG | TAC | ACG | TAT | TCC | GAC | GCC | GTA | TCC | 478 |
| Val | Leu | Cys | Thr | Lys | Cys | Pro | Arg | Tyr | Thr | Tyr | Ser | Asp | Ala | Val | Ser | |
| 145 | | | | | 150 | | | | | 155 | | | | | | |
| TCC | ACG | GAG | ACG | TGT | ACC | TCG | TCG | TTT | AAC | TAC | ATC | AGC | GTG | GAA | TTC | 526 |
| Ser | Thr | Glu | Thr | Cys | Thr | Ser | Ser | Phe | Asn | Tyr | Ile | Ser | Val | Glu | Phe | |
| 160 | | | | 165 | | | | | 170 | | | | | 175 | | |
| AAC | CTA | TAT | CCC | GTA | AAC | GAC | ACG | TCT | TGT | ACG | ACG | ACC | GCC | GGA | CCC | 574 |
| Asn | Leu | Tyr | Pro | Val | Asn | Asp | Thr | Ser | Cys | Thr | Thr | Thr | Ala | Gly | Pro | |
| | | | | 180 | | | | | 185 | | | | | 190 | | |
| AAC | GAA | GTG | GTT | AAA | ACG | TCG | GAG | TTC | TCG | GTT | ACG | CTA | AAT | CAC | ACG | 622 |
| Asn | Glu | Val | Val | Lys | Thr | Ser | Glu | Phe | Ser | Val | Thr | Leu | Asn | His | Thr | |
| | | | 195 | | | | | 200 | | | | | 205 | | | |
| GAT | TGT | GAT | CCC | GTC | TTC | CAC | ACG | GAA | TAC | TAC | GGA | ACG | AGC | GGC | AGC | 670 |
| Asp | Cys | Asp | Pro | Val | Phe | His | Thr | Glu | Tyr | Tyr | Gly | Thr | Ser | Gly | Ser | |
| | | 210 | | | | | 215 | | | | | 220 | | | | |
| GAG | GGC | GCG | GGA | GGA | TTC | TTC | ACC | GGG | ATG | GAT | AGG | TAC | CAG | AAT | ACG | 718 |
| Glu | Gly | Ala | Gly | Gly | Phe | Phe | Thr | Gly | Met | Asp | Arg | Tyr | Gln | Asn | Thr | |
| | 225 | | | | | 230 | | | | | 235 | | | | | |
| ACC | AAA | ATG | TGT | ACG | CTT | AAT | ATA | GAG | ATA | CGG | TGC | GTC | GAG | GGA | GAC | 766 |
| Thr | Lys | Met | Cys | Thr | Leu | Asn | Ile | Glu | Ile | Arg | Cys | Val | Glu | Gly | Asp | |
| 240 | | | | | 245 | | | | | 250 | | | | | 255 | |
| GCC | GTG | CGT | ACT | ATA | CCG | AGG | ACG | AGC | GAC | GGG | GTC | GGC | GTC | CTA | TCT | 814 |
| Ala | Val | Arg | Thr | Ile | Pro | Arg | Thr | Ser | Asp | Gly | Val | Gly | Val | Leu | Ser | |
| | | | | 260 | | | | | 265 | | | | | 270 | | |
| CAT | TCG | GAA | ACG | ATT | ACC | GTG | ATA | GGA | GGG | TGC | CTG | TCC | GAC | GTG | AAC | 862 |
| His | Ser | Glu | Thr | Ile | Thr | Val | Ile | Gly | Gly | Cys | Leu | Ser | Asp | Val | Asn | |
| | | | 275 | | | | | 280 | | | | | 285 | | | |
| GTA | GAT | ATC | GAG | TAC | AGC | GAC | AGT | AAT | CAT | CCC | GAG | GAG | GTC | GAC | GAC | 910 |
| Val | Asp | Ile | Glu | Tyr | Ser | Asp | Ser | Asn | His | Pro | Glu | Glu | Val | Asp | Asp | |
| | | 290 | | | | | 295 | | | | | 300 | | | | |
| TTC | GTG | GAA | TAC | CAT | TGG | GGT | ACA | CGC | CTC | CGT | CTC | TTT | CCC | TCA | CCC | 958 |
| Phe | Val | Glu | Tyr | His | Trp | Gly | Thr | Arg | Leu | Arg | Leu | Phe | Pro | Ser | Pro | |
| | 305 | | | | | 310 | | | | | 315 | | | | | |
| AAA | CGA | TGT | AGA | CTC | GTT | TCA | TAGATTACGG | ATTTTCTTCT | AGTTAAATTC | | | | | | | 1009 |
| Lys | Arg | Cys | Arg | Leu | Val | Ser | | | | | | | | | | |
| 320 | | | | | 325 | | | | | | | | | | | |
| TTAAAAAAAA | GTCGAATTAT | AATAAAACGT | GGGCGTATAG | AAGAACTCTA | TCATG | | | | | | | | | | | 1064 |

( 2 ) INFORMATION FOR SEQ ID NO:4:

( i ) SEQUENCE CHARACTERISTICS:

(A) LENGTH: 326 amino acids
(B) TYPE: amino acid
(D) TOPOLOGY: linear (ii) MOLECULE TYPE: protein (xi) SEQUENCE DESCRIPTION: SEQ ID NO:4:

```
Met Phe Arg Leu Thr Leu Leu Leu Ala Tyr Val Ala Cys Val Tyr Gly
 1               5                  10                  15

Gly Gly Ala Pro Tyr Gly Ala Asp Arg Gly Lys Cys Arg Gly Asn Asp
             20                  25                  30

Tyr Glu Lys Asp Gly Leu Cys Cys Thr Ser Cys Pro Pro Gly Ser Tyr
         35                  40                  45

Ala Ser Arg Leu Cys Gly Pro Gly Ser Asp Thr Val Cys Ser Pro Cys
     50                  55                  60

Lys Asn Glu Thr Phe Thr Ala Ser Thr Asn His Ala Pro Ala Cys Val
 65                  70                  75                  80

Ser Cys Arg Gly Arg Cys Thr Gly His Leu Ser Glu Ser Gln Ser Cys
                 85                  90                  95

Asp Lys Thr Arg Asp Arg Val Cys Asp Cys Ser Ala Gly Asn Tyr Cys
             100                 105                 110

Leu Leu Lys Gly Gln Glu Gly Cys Arg Ile Cys Ala Pro Lys Thr Lys
             115                 120                 125

Cys Pro Ala Gly Tyr Gly Val Ser Gly His Thr Arg Thr Gly Asp Val
     130                 135                 140

Leu Cys Thr Lys Cys Pro Arg Tyr Thr Tyr Ser Asp Ala Val Ser Ser
145                 150                 155                 160

Thr Glu Thr Cys Thr Ser Ser Phe Asn Tyr Ile Ser Val Glu Phe Asn
                 165                 170                 175

Leu Tyr Pro Val Asn Asp Thr Ser Cys Thr Thr Thr Ala Gly Pro Asn
             180                 185                 190

Glu Val Val Lys Thr Ser Glu Phe Ser Val Thr Leu Asn His Thr Asp
             195                 200                 205

Cys Asp Pro Val Phe His Thr Glu Tyr Tyr Gly Thr Ser Gly Ser Glu
     210                 215                 220

Gly Ala Gly Gly Phe Phe Thr Gly Met Asp Arg Tyr Gln Asn Thr Thr
225                 230                 235                 240

Lys Met Cys Thr Leu Asn Ile Glu Ile Arg Cys Val Glu Gly Asp Ala
                 245                 250                 255

Val Arg Thr Ile Pro Arg Thr Ser Asp Gly Val Gly Val Leu Ser His
             260                 265                 270

Ser Glu Thr Ile Thr Val Ile Gly Gly Cys Leu Ser Asp Val Asn Val
         275                 280                 285

Asp Ile Glu Tyr Ser Asp Ser Asn His Pro Glu Glu Val Asp Asp Phe
     290                 295                 300

Val Glu Tyr His Trp Gly Thr Arg Leu Arg Leu Phe Pro Ser Pro Lys
305                 310                 315                 320

Arg Cys Arg Leu Val Ser
                 325
```

(2) INFORMATION FOR SEQ ID NO:5:

(i) SEQUENCE CHARACTERISTICS:
(A) LENGTH: 1065 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Cowpox virus (i x) FEATURE:
    (A) NAME/KEY: CDS
    (B) LOCATION: 1..1065

(x i) SEQUENCE DESCRIPTION: SEQ ID NO:5:

| | | | | | | | | | | | | | | | | |
|---|---|---|---|---|---|---|---|---|---|---|---|---|---|---|---|---|
| ATG | AAG | TCA | TAT | ATA | TTG | CTA | TTG | CTG | CTT | TCA | TGT | ATA | ATC | ATA | ATA | 48 |
| Met | Lys | Ser | Tyr | Ile | Leu | Leu | Leu | Leu | Leu | Ser | Cys | Ile | Ile | Ile | Ile | |
| 1 | | | | 5 | | | | | 10 | | | | | 15 | | |
| AAC | AGC | GAT | ATA | ACA | CCG | CAT | GAA | CCA | TCC | AAC | GGA | AAG | TGT | AAA | GAC | 96 |
| Asn | Ser | Asp | Ile | Thr | Pro | His | Glu | Pro | Ser | Asn | Gly | Lys | Cys | Lys | Asp | |
| | | | 20 | | | | 25 | | | | | 30 | | | | |
| AAC | GAA | TAC | AAA | CGC | CAT | CAT | CTA | TGT | TGT | TTA | TCG | TGT | CCT | CCG | GGA | 144 |
| Asn | Glu | Tyr | Lys | Arg | His | His | Leu | Cys | Cys | Leu | Ser | Cys | Pro | Pro | Gly | |
| | | 35 | | | | | 40 | | | | | 45 | | | | |
| ACA | TAC | GCT | TCC | AGA | TTA | TGC | GAT | AGC | AAG | ACT | AAC | ACA | AAC | ACA | CAA | 192 |
| Thr | Tyr | Ala | Ser | Arg | Leu | Cys | Asp | Ser | Lys | Thr | Asn | Thr | Asn | Thr | Gln | |
| | 50 | | | | | 55 | | | | | 60 | | | | | |
| TGT | ACG | CCG | TGT | GCG | TCG | GAC | ACC | TTT | ACG | TCT | CGC | AAT | AAT | CAT | TTA | 240 |
| Cys | Thr | Pro | Cys | Ala | Ser | Asp | Thr | Phe | Thr | Ser | Arg | Asn | Asn | His | Leu | |
| 65 | | | | | 70 | | | | | 75 | | | | | 80 | |
| CCC | GCT | TGT | CTA | AGT | TGT | AAC | GGA | AGA | TGC | GAT | AGT | AAT | CAG | GTA | GAG | 288 |
| Pro | Ala | Cys | Leu | Ser | Cys | Asn | Gly | Arg | Cys | Asp | Ser | Asn | Gln | Val | Glu | |
| | | | | 85 | | | | | 90 | | | | | 95 | | |
| ACG | CGA | TCG | TGT | AAC | ACG | ACT | CAC | AAT | AGA | ATC | TGT | GAT | TGT | GCT | CCC | 336 |
| Thr | Arg | Ser | Cys | Asn | Thr | Thr | His | Asn | Arg | Ile | Cys | Asp | Cys | Ala | Pro | |
| | | | 100 | | | | | 105 | | | | | 110 | | | |
| GGA | TAT | TAT | TGT | TTT | CTC | AAA | GGA | TCA | TCC | GGA | TGC | AAG | GCA | TGT | GTT | 384 |
| Gly | Tyr | Tyr | Cys | Phe | Leu | Lys | Gly | Ser | Ser | Gly | Cys | Lys | Ala | Cys | Val | |
| | | 115 | | | | | 120 | | | | | 125 | | | | |
| TCC | CAA | ACA | AAG | TGT | GGA | ATA | GGA | TAC | GGA | GTA | TCC | GGA | CAC | ACG | CCT | 432 |
| Ser | Gln | Thr | Lys | Cys | Gly | Ile | Gly | Tyr | Gly | Val | Ser | Gly | His | Thr | Pro | |
| | 130 | | | | | 135 | | | | | 140 | | | | | |
| ACC | GGA | GAC | GTC | GTC | TGT | TCT | CCG | TGT | GGT | CTC | GGA | ACA | TAT | TCT | CAC | 480 |
| Thr | Gly | Asp | Val | Val | Cys | Ser | Pro | Cys | Gly | Leu | Gly | Thr | Tyr | Ser | His | |
| 145 | | | | | 150 | | | | | 155 | | | | | 160 | |
| ACC | GTC | TCT | TCC | GTA | GAT | AAA | TGC | GAA | CCC | GTA | CCC | AGT | AAT | ACC | TTT | 528 |
| Thr | Val | Ser | Ser | Val | Asp | Lys | Cys | Glu | Pro | Val | Pro | Ser | Asn | Thr | Phe | |
| | | | | 165 | | | | | 170 | | | | | 175 | | |
| AAC | TAT | ATC | GAT | GTG | GAA | ATT | AAT | CTG | TAT | CCC | GTC | AAC | GAC | ACA | TCG | 576 |
| Asn | Tyr | Ile | Asp | Val | Glu | Ile | Asn | Leu | Tyr | Pro | Val | Asn | Asp | Thr | Ser | |
| | | | 180 | | | | | 185 | | | | | 190 | | | |
| TGT | ACT | CGG | ACG | ACC | ACT | ACC | GGT | CTC | AGT | GAA | TCC | ATC | TCA | ACT | TCG | 624 |
| Cys | Thr | Arg | Thr | Thr | Thr | Thr | Gly | Leu | Ser | Glu | Ser | Ile | Ser | Thr | Ser | |
| | | 195 | | | | | 200 | | | | | 205 | | | | |
| GAA | CTA | ACG | ATT | ACT | ATG | AAT | CAT | AAA | GAC | TGC | GAT | CCC | GTC | TTT | CGT | 672 |
| Glu | Leu | Thr | Ile | Thr | Met | Asn | His | Lys | Asp | Cys | Asp | Pro | Val | Phe | Arg | |
| | 210 | | | | | 215 | | | | | 220 | | | | | |
| AAT | GGA | TAC | TTC | TCC | GTT | CTT | AAT | GAG | GTA | GCA | ACT | TCA | GGG | TTC | TTT | 720 |
| Asn | Gly | Tyr | Phe | Ser | Val | Leu | Asn | Glu | Val | Ala | Thr | Ser | Gly | Phe | Phe | |
| 225 | | | | | 230 | | | | | 235 | | | | | 240 | |
| ACA | GGA | CAA | AAT | AGA | TAT | CAG | AAT | ATT | TCA | AAG | GTA | TGC | ACT | CTG | AAT | 768 |
| Thr | Gly | Gln | Asn | Arg | Tyr | Gln | Asn | Ile | Ser | Lys | Val | Cys | Thr | Leu | Asn | |
| | | | | 245 | | | | | 250 | | | | | 255 | | |

| | | | | | | | | | | | | | | | | |
|---|---|---|---|---|---|---|---|---|---|---|---|---|---|---|---|---|
| TTC | GAG | ATT | AAA | TGT | AAT | AAC | AAA | GAT | TCT | TAT | TCT | TCC | TCC | AAA | CAG | 816 |
| Phe | Glu | Ile | Lys | Cys | Asn | Asn | Lys | Asp | Ser | Tyr | Ser | Ser | Ser | Lys | Gln | |
| | | | 260 | | | | 265 | | | | | | 270 | | | |
| TTA | ACG | AAA | ACA | AAG | AAT | GAT | GAC | GAC | TCC | ATC | ATG | CCG | CAT | TCG | GAA | 864 |
| Leu | Thr | Lys | Thr | Lys | Asn | Asp | Asp | Asp | Ser | Ile | Met | Pro | His | Ser | Glu | |
| | | 275 | | | | | 280 | | | | | 285 | | | | |
| TCG | GTA | ACT | CTA | GTG | GGC | GAC | TGT | CTA | TCC | AGC | GTC | GAC | ATC | TAT | ATA | 912 |
| Ser | Val | Thr | Leu | Val | Gly | Asp | Cys | Leu | Ser | Ser | Val | Asp | Ile | Tyr | Ile | |
| | 290 | | | | | 295 | | | | | 300 | | | | | |
| CTA | TAT | AGT | AAT | ACC | AAT | ACT | CAA | GAC | TAC | GAA | ACT | GAT | ACA | ATC | TCT | 960 |
| Leu | Tyr | Ser | Asn | Thr | Asn | Thr | Gln | Asp | Tyr | Glu | Thr | Asp | Thr | Ile | Ser | |
| 305 | | | | | 310 | | | | | 315 | | | | | 320 | |
| TAT | CAT | GTG | GGT | AAT | GTT | CTC | GAT | GTC | GAT | AGC | CAT | ATG | CCC | GGT | AGG | 1008 |
| Tyr | His | Val | Gly | Asn | Val | Leu | Asp | Val | Asp | Ser | His | Met | Pro | Gly | Arg | |
| | | | | 325 | | | | | 330 | | | | | 335 | | |
| TGC | GAT | ACA | CAT | AAA | CTG | ATT | ACT | AAT | TCC | AAT | TCC | CAG | TAT | CCC | ACC | 1056 |
| Cys | Asp | Thr | His | Lys | Leu | Ile | Thr | Asn | Ser | Asn | Ser | Gln | Tyr | Pro | Thr | |
| | | | 340 | | | | | 345 | | | | | 350 | | | |
| CAC | TTT | TTA | | | | | | | | | | | | | | 1065 |
| His | Phe | Leu | | | | | | | | | | | | | | |
| | | 355 | | | | | | | | | | | | | | |

( 2 ) INFORMATION FOR SEQ ID NO:6:

( i ) SEQUENCE CHARACTERISTICS:
        ( A ) LENGTH: 355 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Met | Lys | Ser | Tyr | Ile | Leu | Leu | Leu | Leu | Leu | Ser | Cys | Ile | Ile | Ile | Ile |
| 1 | | | | 5 | | | | | 10 | | | | | 15 | |
| Asn | Ser | Asp | Ile | Thr | Pro | His | Glu | Pro | Ser | Asn | Gly | Lys | Cys | Lys | Asp |
| | | | 20 | | | | | 25 | | | | | 30 | | |
| Asn | Glu | Tyr | Lys | Arg | His | His | Leu | Cys | Cys | Leu | Ser | Cys | Pro | Pro | Gly |
| | | 35 | | | | | 40 | | | | | 45 | | | |
| Thr | Tyr | Ala | Ser | Arg | Leu | Cys | Asp | Ser | Lys | Thr | Asn | Thr | Asn | Thr | Gln |
| | 50 | | | | | 55 | | | | | 60 | | | | |
| Cys | Thr | Pro | Cys | Ala | Ser | Asp | Thr | Phe | Thr | Ser | Arg | Asn | Asn | His | Leu |
| 65 | | | | | 70 | | | | | 75 | | | | | 80 |
| Pro | Ala | Cys | Leu | Ser | Cys | Asn | Gly | Arg | Cys | Asp | Ser | Asn | Gln | Val | Glu |
| | | | | 85 | | | | | 90 | | | | | 95 | |
| Thr | Arg | Ser | Cys | Asn | Thr | Thr | His | Asn | Arg | Ile | Cys | Asp | Cys | Ala | Pro |
| | | | 100 | | | | | 105 | | | | | 110 | | |
| Gly | Tyr | Tyr | Cys | Phe | Leu | Lys | Gly | Ser | Ser | Gly | Cys | Lys | Ala | Cys | Val |
| | | 115 | | | | | 120 | | | | | 125 | | | |
| Ser | Gln | Thr | Lys | Cys | Gly | Ile | Gly | Tyr | Gly | Val | Ser | Gly | His | Thr | Pro |
| | 130 | | | | | 135 | | | | | 140 | | | | |
| Thr | Gly | Asp | Val | Val | Cys | Ser | Pro | Cys | Gly | Leu | Gly | Thr | Tyr | Ser | His |
| 145 | | | | | 150 | | | | | 155 | | | | | 160 |
| Thr | Val | Ser | Ser | Val | Asp | Lys | Cys | Glu | Pro | Val | Pro | Ser | Asn | Thr | Phe |
| | | | | 165 | | | | | 170 | | | | | 175 | |
| Asn | Tyr | Ile | Asp | Val | Glu | Ile | Asn | Leu | Tyr | Pro | Val | Asn | Asp | Thr | Ser |
| | | | 180 | | | | | 185 | | | | | 190 | | |
| Cys | Thr | Arg | Thr | Thr | Thr | Thr | Gly | Leu | Ser | Glu | Ser | Ile | Ser | Thr | Ser |
| | | 195 | | | | | 200 | | | | | 205 | | | |

| | | | | | | | | | | | | | | |
|---|---|---|---|---|---|---|---|---|---|---|---|---|---|---|
| Glu | Leu | Thr | Ile | Thr | Met | Asn | His | Lys | Asp | Cys | Asp | Pro | Val | Phe | Arg |
| | 210 | | | | 215 | | | | | 220 | | | | | |
| Asn | Gly | Tyr | Phe | Ser | Val | Leu | Asn | Glu | Val | Ala | Thr | Ser | Gly | Phe | Phe |
| 225 | | | | | 230 | | | | | 235 | | | | | 240 |
| Thr | Gly | Gln | Asn | Arg | Tyr | Gln | Asn | Ile | Ser | Lys | Val | Cys | Thr | Leu | Asn |
| | | | | 245 | | | | | 250 | | | | | 255 | |
| Phe | Glu | Ile | Lys | Cys | Asn | Asn | Lys | Asp | Ser | Tyr | Ser | Ser | Ser | Lys | Gln |
| | | | 260 | | | | | 265 | | | | | 270 | | |
| Leu | Thr | Lys | Thr | Lys | Asn | Asp | Asp | Ser | Ile | Met | Pro | His | Ser | Glu |
| | | 275 | | | | 280 | | | | | 285 | | | |
| Ser | Val | Thr | Leu | Val | Gly | Asp | Cys | Leu | Ser | Ser | Val | Asp | Ile | Tyr | Ile |
| | 290 | | | | | 295 | | | | | 300 | | | | |
| Leu | Tyr | Ser | Asn | Thr | Asn | Thr | Gln | Asp | Tyr | Glu | Thr | Asp | Thr | Ile | Ser |
| 305 | | | | | 310 | | | | | 315 | | | | | 320 |
| Tyr | His | Val | Gly | Asn | Val | Leu | Asp | Val | Asp | Ser | His | Met | Pro | Gly | Arg |
| | | | | 325 | | | | | 330 | | | | | 335 | |
| Cys | Asp | Thr | His | Lys | Leu | Ile | Thr | Asn | Ser | Asn | Ser | Gln | Tyr | Pro | Thr |
| | | | 340 | | | | | 345 | | | | | 350 | | |
| His | Phe | Leu |
| | | 355 |

(2) INFORMATION FOR SEQ ID NO:7:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: oligonucleotide1

(xi) SEQUENCE DESCRIPTION: SEQ ID NO:7:

GTACCGCCAC CATGCTTCGT TTAATTGCAC TATCATATGA ATATGGATTC AA    52

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: oligonucleotide1

(xi) SEQUENCE DESCRIPTION: SEQ ID NO:8:

CTAGTAGTGC AATTAAACGA AGCATGGTGG CG    32

(2) INFORMATION FOR SEQ ID NO:9:

(i) SEQUENCE CHARACTERISTICS:

-continued (A) LENGTH: 74 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: oligonucleotide1

(xi) SEQUENCE DESCRIPTION: SEQ ID NO:9:

```
CCTTGCGGCC  GCCACCATGT  TTCGTTTAAC  GCTACTACTC  ATTTATAGGA  GATGTGTCAT    60

ATGAATATGG  TCAA                                                          74
```

(2) INFORMATION FOR SEQ ID NO:10:

(i) SEQUENCE CHARACTERISTICS:
    (A) LENGTH: 55 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: oligonucleotide1

(xi) SEQUENCE DESCRIPTION: SEQ ID NO:10:

```
CCTTAGATCT  GTAATCTATG  AAACGAGTCT  ACATTCATAT  GAATATGGAT  TCTAA          55
```

ISOLATED VIRAL PROTEIN TNF ANTAGONISTS

CROSS-REFERENCE TO RELATED APPLICATION

This application is a continuation of U.S. application Ser. No. 07/963,330, filed Oct. 19, 1992, now abandoned, which is a continuation-in-part of U.S. application Ser. No. 07/507,213, filed Apr. 9, 1990, now abandoned.

BACKGROUND OF THE INVENTION

The present invention relates generally to the field of vital proteins, and more specifically to viral proteins having immunoregulatory activity.

Viruses are infectious particles which contain genetic elements that enable the virus to replicate within a living host cell. By sequencing the genes of viruses and analyzing the DNA sequence, it has been possible to identify many open reading frames (ORFs) comprising long stretches of triplet codons beginning with a translation-initiation codon (preceded by a ribosomal binding site) and uninterrupted by a translational stop codon. Most ORFs in viruses, however, have not been shown to code proteins. For example, the genomic organization and DNA sequence of several ORFs from the telomeric region of Shope fibroma virus (SFV) have recently been characterized (Upton et al.,Virology 160:20 (1987)). Although it has been shown that these ORFs are transcriptionally active and code for mRNAs, no proteins encoded by these mRNAs have yet been identified or isolated, nor has any biological function for the putative proteins (as surmised from the ORF) been identified. Similarly, the DNA sequence of telomeric region of the myxoma virus has been obtained and several DRFs identified; however, no protein encoded by these ORFs has been identified, isolated or characterized.

The present invention identifies a specific class of vital proteins having innnunosuppressive activity, and provides a method for identifying and isolating such viral proteins. The invention also provides pharmaceutical compositions for regulating immune responses.

SUMMARY OF THE INVENTION

The present invention provides isolated viral proteins having cytokine antagonist activity, and pharmaceutical compositions comprising such vital proteins for regulating immune responses. The present invention also provides processes for preparing isolated viral proteins having cytokine antagonist activity.

The isolated viral proteins of this invention are similar to cytokine binding proteins, such as the extracellular region of a cytokine receptor, and are capable of binding a cytokine and preventing the cytokine from binding to its receptor. The ability of such viral proteins to mimic the activity of a cytokine receptor (and thereby downregulate specific immune responses) enables the viral protein to circumvent the anti-viral defense mechanisms of the host organisms and confers a selective advantage to the virus. The viral proteins of the present invention can be used to regulate immune responses in a therapeutic setting.

The present invention specifically provides isolated Shope fibroma virus (SFV) T2 protein, which is an expression product of the SFV T2 open reading frame, and isolated myxoma virus (MV) T2 protein, which is an expression product of the myxoma T2 open reading frame. Both SFV T2 protein and myxoma T2 protein have TNF antagonist activity. The equivalent ORF (or locus) in cowpox is referred to as D2. The present invention also specifically provides isolated Cowpox virus (CPV) T2-equivalent protein, which is an expression product of the CPV T2-equivalent open reading frame, and has TNF antagonist activity. Other poxviruses have loci equivalent to the T2 locus of SFV or myxoma virus.

These and other aspects of the present invention will become evident upon reference to the following detailed description of the invention.

BRIEF DESCRIPTION OF THE SEQUENCE LISTING

SEQ ID NO: 1 and SEQ ID NO:2 depict the cDNA sequence and derived amino acid sequence of the Shope fibroma virus (SFV) T2 open reading frame (ORF). The SFV T2 ORF extends from nucleotide 1332 to 2306 and encodes an amino acid sequence designated as the c-phase reading frame.

SEQ ID NO:3 and SEQ ID NO:4 depict the cDNA sequence and derived antino acid sequence of the myxoma virus T2ORF. The myxoma T2ORF extends from nucleotide 2 to 979 and encodes an amino acid sequence designated as the b-phase reading frame.

SEQ ID NO:5 and SEQ ID NO:6 depict the cDNA sequence and derived amino acid sequence of the Cowpox virus (CPV) D2 (T2-equivalent) ORF. The CPV D2ORF extends from nucleotide 1 to 1065 and encodes an amino acid sequence designated as the c-phase reading frame.

DETAILED DESCRIPTION OF THE INVENTION

The immune system protects the human body from infection and disease through the interaction of specialized white blood cells which recognize and destroy invading microbes and diseased cells. White blood cells, including T cells, B cells, granulocytes and macrophages, are controlled and coordinated by specific proteins known as cytokines, which direct the development, proliferation, function and effectiveness of these cells. Cytokines act upon immune cells by contacting and attaching (i.e., binding) specific proteins called cytokine receptors which are located on immune cell surfaces. The binding of a cytokine to its specific receptor initiates a complex series of events within the responsive cell which translates the cytokine's signal to that cell. This signal can then stimulate cell division or production of antibodies, enzymes or other cytokines, thereby controlling and coordinating the function of immune cells located throughout the body. In their native configuration, receptor proteins are present as intact human plasma membrane proteins having an extracellular region which binds to a ligand, a hydrophobic transmembrane region which causes the protein to be immobilized within the plasma membrane lipid bilayer, and a cytoplasmic or intracellular region which interacts with proteins and/or chemicals within the cell to deliver a biological signal to effector cells via a cascade of chemical reactions within the cytoplasm of the cell. The extracellular region thus defines a domain of the receptor molecule to which a ligand can bind to transduce a biological signal.

The normal immune response can be weakened by overwhelming infection or other immunosuppressive conditions associated with the development of cancer. Immune system malfunction can also result in autoimmune diseases such as arthritis and diabetes, which result when a misdirected immune response destroys joint tissues or pancreatic cells. Transplant patients frequently suffer organ rejection, in which the immune system attacks the transplanted organ as a foreign body. In other immune disorders, the immune system overreacts to normal encounters with foreign substances, resulting in allergic conditions or asthma. Byproducts of severe immune responses can also be harmful, for example, in the inflammatory conditions know as cachexia and septic shock. Furthermore, cytokinedirected accumulation of white blood cells in response to infection can lead to inflammatory conditions which can exacerbate the severity of lung disease conditions such as emphysema.

Such misdirected or inappropriate immune responses may be counteracted by cytokine antagonists, which bind to the cytokine and prevent the cytokine from binding to its receptor, thereby inhibiting the initiation of an immune response.

The present invention relates to viral proteins which are capable of modulating the activity of cytokines by acting as cytokine antagonists. The viral proteins of the present invention have a sequence of amino acids which is similar to the ligand-binding region of a cytokine receptor (e.g., the extracellular region of the receptor) or to a soluble cytokine receptor and is capable of binding to the cytokine and preventing the cytokine from binding to its receptor.

Definitions

As used herein, the term "vital protein" refers to proteins encoded by RNA, DNA, mRNA or cDNA isolated or otherwise derived from a viral source.

"Isolated", as used in the context of the present invention to define the purity of viral proteins, refers to proteins which are substantially free of other human or viral proteins of natural or endogenous origin and contains less than about 1% by mass of protein contaminants residual of production processes. Such compositions, however, can contain other proteins added as stabilizers, carriers, excipients or co-therapeutics. Isolated viral proteins are detectable as a single protein band in a polyacrylamide gel by silver staining.

A "cytokine" is a specific protein which directs the development, proliferation, function and effectiveness of cells of the immune system. Specific examples of "cytokines" include, but are not limited to, the interleukins (e.g., IL-1, IL-2, IL-3, IL-4, IL-5, IL-6, IL-7, IL-8), interferon (IFNα and IFNβ), tumor necrosis factor (TNFα and TNF 13) and various growth factors, such as GM-CSF, G-CSF, and CSF-1. Each of the above cytokines transduces a biological signal by binding to a receptor molecule specific to the cytokine.

A viral protein having "cytokine antagonist activity" inhibits, counteracts or neutralizes the biological activity of a cytokine. Cytokine antagonist activity may be effected by means of the viral protein sterically hindering the binding of a cytokine to its receptor, thereby preventing cytokine signal transduction. For example, a viral protein can sterically hinder the binding of a cytokine to its receptor by binding the cytokine or its receptor at or near a site required for cytokine/receptor binding. The viral protein thus physically prevents the cytokine and receptor from interacting and transducing a biological signal. Specific examples of viral proteins having cytokine antagonist activity include polypeptides encoded by the SFV T2 open reading frame and the myxoma virus T2 opening reading frame, designated herein as SFV T2 protein and myxoma virus T2 protein, respectively. The DNA sequence of the open reading frame encoding SFV T2 protein and the amino acid sequence of SFV T2 protein is set forth in SEQ ID NO: 1. The DNA sequence of the open reading frame encoding myxoma T2 protein and the amino acid sequence of myxoma T2 protein is set forth in SEQ ID NO:3.

The phrase "T2" generally refers to a locus, or ORF, present in SFV and myxoma virus. Other poxviruses also have ORFs that are equivalent to the T2ORFs of SFV and myxoma virus. The nomenclature used with other poxviruses may be different than that used for SFV and myxoma virus; for example, the T2-equivalent loci of cowpox virus (CPV) is referred to as D2. The DNA sequence of the ORF encoding CPV T2-equivalent protein and the amino acid sequence of CPV T2-equivalent protein is set forth in SEQ D NO.:5. The T2-equivalent ORFs of other poxviruses will have amino acid and nucleotide sequence similarity to the T2ORFs of SFV and myxoma and the T2-equivalent ORF of CPV, and are likely to have similar cytokine antagonist activity.

SFV T2, myxoma T2, and CPV T2-equivalent protein are TNF antagonists. Tumor necrosis factor-α (TNFα, also known as cachectin) and tumor necrosis factor-β (TNFβ, also known as lymphotoxin) are homologous mammalian endogenous secretory proteins capable of inducing a wide variety of effects on a large number of cell types. The great similarities in the structural and functional characteristics of these two cytokines have resulted in their collective description as "TNF." Complementary DNA clones encoding TNFa (Pennica et al., *Nature* 312:724, 1984) and TNFβ (Gray et al., *Nature* 312:721, 1984) have been isolated.

TNF initiates its biological effect on cells by binding to specific TNF receptor protein expressed on the plasma membrane of a TNF-responsive cell. It is believed that TNFα and TNFβ share a common receptor. The amino acid sequences of SFV T2, myxoma T2, and CPV T2-equivalent protein are similar to the extracellular region of the receptor to which TNF binds, and mimic the TNF receptor by binding to TNF. SFV T2, myxoma T2, and CPV T2-equivalent protein thus inhibit binding of TNF to TNF receptor: Proteins encoded by T2-equivalent ORFs in other poxviruses will have amino acid sequences similar to the extracellular region of the receptor to which TNF binds, and will also mimic the TNF receptor by binding to TNF and thus inhibit binding of TNF to TNF receptor. Because of its ability to inhibit binding of TNF to TNF receptor, isolated SFV T2, myxoma T2, and CPV T2-equivalent protein compositions will be useful in diagnostic assays for TNF, as well as in raising antibodies to SFV T2, myxoma T2, and CPV T2equivalent protein for use in diagnosis and therapy. In addition, purified SFV T2, myxoma T2, and CPV T2-equivalent protein compositions may be used directly in therapy to bind or scavenge TNF, thereby providing a means for regulating the immune activities of TNF. Isolated T2-equivalent protein compositions of other poxviruses will have similar utilities. In order to study the structural and biological characteristics of SFV T2, myxoma T2, CPV T2-equivalent and other poxvirus T2-equivalent proteins, and the roles played by SFV T2, myxoma T2, CPV T2-equivalent and T2-equivalent proteins of other poxviruses in the responses of various cell populations to viral infection by SFV, MV, CPV, and other poxviruses, or to use SFV T2, myxoma T2, CPV T2-equivalent and other poxvirus T2equivalent proteins effectively in therapy, diagnosis, or assay, purified compositions of SFV T2, myxoma T2, CPV T2-equivalent and other poxvirus T2-equivalent proteins are needed. Such compositions, however, are obtainable in practical yields only by cloning and expressing genes encoding the receptors using recombinant DNA technology.

The terms "TNF receptor" and "TNF-R" refer to proteins having amino acid sequences of the native mammalian TNF receptor amino acid sequences.

A "soluble cytokine receptor", as used in the context of the present invention, refers to a protein, or a substantially equivalent analog, having an amino acid sequence corresponding to the extracellular region of a native cytokine receptor, for example polypeptides having the amino acid sequences substantially equivalent to the extracellular region of TNF receptor. Because soluble proteins are devoid of a transmembrane region, they are secreted from the host cell in which they are produced. Viral proteins having an amino acid sequence sufficiently similar to the extracellular region of a cytokine receptor or to a soluble cytokine receptor will retain the ability to bind the cytokine and inhibit the ability of the cytokine to transduce a signal via cell surface bound cytokine receptor proteins. When administered in therapeutic formulations, the viral proteins circulate in the body and bind to circulating cytokine molecules, preventing interaction of the cytokine with natural cytokine receptors and inhibiting transduction of cytokine-mediated biological signals, such as immune or inflammatory responses.

A viral protein has "cytokine antagonist activity" if the viral protein has a sequence of amino acids "sufficiently similar" to either the extracellular region of a cytokine receptor or to a soluble receptor that the vital protein is capable of inhibiting binding of the cytokine receptor to its ligand, thereby inhibiting cytokine signal transduction. Assays for determining cytokine binding inhibition are described below in Example 1. Inhibition of cytokine signal transduction can be determined by transfecting cells with recombinant cytokine receptor DNAs to obtain recombinant receptor expression. The cells are then contacted with the cytokine ligand and the resulting metabolic effects examined. If an effect results which is attributable to the action of the ligand, then the recombinant receptor has signal transducing activity. Exemplary procedures for determining whether a polypeptide has signal transducing activity are disclosed by Idzerda et al., *J. Exp. Med.* 171:861 (1990); Curtis et al., *Proc. Natl. Acad. Sci. USA* 86:3045 (1989); Prywes et al., *EMBO J.* 5:2179 (1986); and Chou et al., *J. Biol. Chem.* 262:1842 (1987). Alternatively, primary cells of cell lines which express an endogenous cytokine receptor and have a detectable biological response to the cytokine could also be utilized. Such procedures. are used as controls for assaying inhibition of signal transduction by the viral protein cytokine antagonists of the present invention.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., *E. coli*, will be free of glycan. Protein expressed in yeast may have a glycosylation pattern different from that expressed in mammalian cells.

"Biologically active," as used throughout the specification as a characteristic of a cytokine or a cytokine receptor, means that a particular molecule shares sufficient amino acid sequence similarity with the cytokine or receptor to be capable of binding detectable quantities of the cytokine, or cross-reacting with anti-cytokine receptor antibodies raised against the cytokine from natural (i.e., nonrecombinant) sources.

"DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

The viral proteins of the present invention having cytokine antagonist activity are identified by isolating and then analyzing a vital protein, RNA, DNA, mRNA or cDNA to provide an amino acid sequence of the vital protein. The amino acid sequence of the viral protein is then compared with the amino acid sequence of a cytokine or cytokine receptor and those viral proteins are selected and isolated which have a sequence of amino acids sufficiently similar to an extracellular region of a cytokine receptor or a soluble cytokine receptor that the viral protein is capable of inhibiting binding of the cytokine receptor to its ligand. Alternatively, viral proteins can be selected and isolated which have a sequence similar to a cytokine and are capable of binding to a cytokine receptor (without transducing a cytokine signal) and inhibiting binding of the cytokine to its receptor.

Alternative methods for identifying viral proteins having cytokine antagonist activity include selecting a vital RNA, DNA, mRNA or cDNA capable of hybridization under moderately stringent conditions (50° C., 2×SSC) to DNA or cDNA clones encoding a cytokine binding protein and isolating the protein. DNA or RNA sequences capable of hybridization to DNA clones encoding a cytokine binding protein under such conditions would be expected to be sufficiently similar to the cytokine binding protein to be capable of binding to the cytokine and inhibiting binding of the cytokine to its receptor.

Proteins and Analogs

The present invention provides isolated proteins having cytokine antagonist activity. Such proteins are substantially free of contaminating endogenous materials and, optionally, without associated native-pattern glycosylation. Derivatives of the viral proteins within the scope of the invention also include various structural forms of the primary protein which retain biological activity. Due to the presence of ionizable amino and carboxyl groups, for example, a protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini. Other derivatives of the protein within the scope of this invention include covalent or aggregative conjugates of the protein or its fragments with other proteins or polypeptides, such as by synthesis in recombinant culture as N-terminal or C-terminal fusions. For example, the conjugated peptide may be a a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader). Protein fusions can comprise peptides added to facilitate purification or identification of viral proteins (e.g., poly-His). The amino acid sequence of the vital proteins can also be linked to the peptide Asp—Tyr—Lys—Asp—Asp—Asp—Asp—Lys (DYKDDDDK) (Hopp et al., *Bio/Technology* 6:1204,1988.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp—Lys pairing. Fusion proteins capped with this peptide may also be resistant to intracellular degradation in *E. coli*.

Protein derivatives may also be used as immunogens, reagents in receptor-based immunoassays, or as binding agents for affinity purification procedures of cytokines or other binding ligands. Viral protein derivatives may also be obtained by cross-linking agents, such as M-maleimidobenzoyl succinimide ester and N-hydroxysuccinimide, at cysteine and lysine residues. Proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, proteins may be used to selectively bind (for purposes of assay or purification) antibodies raised against the viral protein or against cytokine receptors which are similar to the viral protein.

The present invention also includes vital proteins with or without associated native-pattern glycosylation. Proteins expressed in yeast or mammalian expression systems, e.g., COS-7 cells, may be similar or slightly different in molecular weight and glycosylation pattern than the native molecules, depending upon the expression system. Expression of viral DNAs in bacteria such as *E. coli* provides non-glycosylated molecules. Functional mutant analogs of viral protein having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn—$A_1$—Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between A1 and Z, or an amino acid other than Asn between Asn and $A_1$.

Viral protein derivatives may also be obtained by mutations of the native vital proteins or its subunits. A vital protein mutant, as referred to herein, is a polypeptide homologous to a viral protein but which has an amino acid sequence different from the native vital protein because of a deletion, insertion or substitution.

Bioequivalent analogs of vital proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physicochemical characteristics resembling those of the residue to be replaced. Similarly, when a deletion or insertion strategy is adopted, the potential effect of the deletion or insertion on biological activity should be considered. Subunits of vital proteins may be constructed by deleting terminal or internal residues or sequences.

Mutations in nucleotide sequences constructed for expression of analog viral proteins must, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed viral protein mutants screened for the desired activity.

Not all mutations in the nucleotide sequence which encodes a viral protein will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed, by Walder et al. (*Gene* 42:133, 1986); Bauer et al. (*Gene* 37:73, 1985); Craik (*BioTechniques,* January 1985, 12–19); Smith et al. (*Genetic Engineering: Principles and Methods,* Plenum Press, 1981); and U.S. Pat. Nos. 4,518,584 and 4,737,462 disclose suitable techniques, and are incorporated by reference herein.

Expression of Recombinant Vital Protein Cytokine Antagonists

The proteins of the present invention are preferably produced by recombinant DNA methods by inserting a DNA sequence encoding vital protein into a recombinant expression vector and expressing the DNA sequence in a recombinant microbial expression system under conditions promoting expression.

DNA sequences encoding the proteins provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors include synthetic or cDNA-derived DNA fragments encoding viral proteins or bioequivalent analogs operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

DNA sequences encoding viral proteins which are to be expressed in a microorganism will preferably contain no introns that could prematurely terminate transcription of DNA into mRNA. Due to code degeneracy, there can be considerable variation in nucleotide sequences encoding the same amino acid sequence. Other embodiments include sequences capable of hybridizing under moderately stringent conditions (50° C., 2×SSC) to the DNA sequences encoding viral proteins, and other sequences which are degenerate to those which encode the viral proteins.

Transformed host cells are cells which have been transformed or transfected with expression vectors constructed using recombinant DNA techniques and which contain sequences encoding the viral proteins of the present invention. Transformed host cells may express the desired viral protein, but host cells transformed for purposes of cloning or amplifying viral DNA do not need to express the viral protein. Expressed viral proteins will preferably be secreted into the culture supernatant, depending on the DNA selected, but may be deposited in the cell membrane. Suitable host cells for expression of viral proteins include prokaryotes, yeast or higher eukaryotic cells under the control of appropriate promoters. Prokaryotes include gram negative or gram positive organisms, for example E. coli or bacilli. Higher eukaryotic cells include established cell lines of mammalian origin as described below. Cell-free translation systems could also be employed to produce viral proteins using RNAs derived from the DNA constructs disclosed herein. Appropriate cloning and expression vectors for use with bacterial, fungal, yeast, and mammalian cellular hosts are described by Pouwels et al. (*Cloning Vectors: A Laboratory Manual,* Elsevier, New York, 1985), the relevant disclosure of which is hereby incorporated by reference.

Prokaryotic expression hosts may be used for expression of viral proteins that do not require extensive proteolytic and elisulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtills, Salmonella typhimurium,* and various species within the genera Pseudomonas, Streptomyces, and Staphylococcus, although others may also be employed as a matter of choice.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chen-ficals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase-)and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual,* Cold Spring Harbor Laboratory, p. 412, 1982). A particularly useful bacterial expression system employs the phage $\lambda P_L$ promoter and cI857ts thermolabile repressor. Plasmid vectors available from the American Type Culture Collection which incorporate derivatives of the $\lambda P_L$ promoter include plasmid pHUB2, resident in *E. coli* strain JMB9 (ATCC 37092) and pPLc28, resident in *E. coli* RR1 (ATCC 53082).

Recombinant viral proteins may also be expressed in yeast hosts, preferably from the Saccharomyces species, such as *S. cerevisiae.* Yeast of other genera, such as Pichia or KIuyveromyces may also be employed. Yeast vectors will generally contain an origin of replication from the 2µ yeast plasmid or an autonomously replicating sequence (ARS), promoter, DNA encoding the vital protein, sequences for polyadenylation and transcription termination and a selection gene. Preferably, yeast vectors will include an origin of replication and selectable marker pen-hitting transformation of both yeast and *E. coli*, e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp 1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7: 149, 1968; and Holland et al., *Biochem.* 17:4900, 1978), such as enolase, glyceraldehyde-3-phosphate dehydrogenase, hexokinase, pyruvate decttrboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et Ell. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 µg/ml adenine and 20 µg/ml uracil.

Host strains transformed by vectors comprising the ADH2 promoter may be grown for expression in a rich medium consisting of 1% yeast extract, 2% peptone, and 1% glucose supplemented with 80 µg/ml adenine and 80 µg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included. Further, viral genomic promoter, control and/or signal sequences may be utilized, provided such control sequences are compatible with the host cell chosen. Exemplary vectors can be constructed as disclosed by Okayarea and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

A particularly preferred eukaryotic vector for expression of viral protein DNA is disclosed below in Examples 2 and 6. This vector, referred to as pCAV/NOT, was derived from the mammalian high expression vector pDC201 and contains regulatory sequences from SV40, adenovirus-2, and human cytomegalovirus.

Purified viral proteins or analogs are prepared by culturing suitable host/vector systems to express the recombinant translation products of the DNAs of the present invention, which are then purified from culture media or cell extracts.

For example, supernatants from systems which secrete recombinant protein into culture media can be first concentrated using a commercially available protein concentration filter, for example, an Areicon or Millipore Pellicon ultrafiltration unit. Following the concentration step, the concentrate can be applied to a suitable purification matrix. For example, a suitable affinity matrix can comprise a viral protein or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify a vital protein composition. Some or all of the foregoing purification steps, in various combinations, can also be employed to provide a homogeneous recombinant protein.

Recombinant vital protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant vital protein can be disrupted by any convenient method, including freeze-thaw cycling, sonication, mechanical disruption, or use of cell lysing agents.

Fermentation of yeast which express vital protein as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Viral protein synthesized in recombinant culture is characterized by the presence of non-vital cell components, including proteins, in amounts and of a character which depend upon the purification steps taken to recover the viral protein from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of viral protein free of other proteins which may be normally associated with the viral protein as it is found in nature in its species of origin, e.g. in cells, cell exudates or body fluids.

Administration of Viral Protein Compositions

The present invention provides methods of using therapeutic compositions comprising an effective amount of a viral protein and a suitable diluent and carrier, and methods for regulating an immune response. The use of SFV T2, myxoma T2, CPV T2-equivalent and other poxvirus T2-equivalent proteins in conjunction with soluble cytokine receptors, e.g., TNF receptor, is also contemplated.

For therapeutic use, purified vital protein is administered to a patient, preferably a human, for treatment in a manner appropriate to the indication. Thus, for example, SFV T2, myxoma T2, and CPV T2-equivalent protein compositions administered to suppress immune function can be given by bolus injection, continuous infusion, sustained release from implants, or other suitable technique. Typically, a therapeutic agent will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining the viral protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, oil such factors as the nature and severity of the indication being treated, the desired response, the condition of the patient, and so forth.

SFV T2, myxoma T2, and CPV T2-equivalent proteins are administered for the purpose of inhibiting TNF dependent responses. TNF is used clinically as an antitumor agent and results in severe toxicities. The toxicities associated with the administration of TNF are identical to the effects that the cytokine manifests when it is produced in normal or overactive immune responses. It is believed that TNF produced as a result of the immune response to malignant tissue is a causative factor of cachexia. In addition, TNF is produced in the course of other immune reactions such as the body's response to severe bacterial infection where TNF production can contribute to the development of septic shock. The production of other key cytokines (IL-1, IL-2 or a number of colony stimulating factors) can also induce significant host production of TNF. Thus, the side effects of these cytokines at certain doses administered to human patients have been attributed to the induction of TNF production. Because TNF binds to a specific TNF receptor present on the surface of responsive cells, vital TNF antagonists, such as SFV T2, myxoma T2, and CPV T2-equivalent proteins may be useful as a therapy for cachexia or septic shock or to treat side effects associated with cytokine therapy.

The following examples are offered by way of illustration, and not by way of limitation.

EXAMPLES

Example 1

Binding Assays

A. Radiolabeling of TNFα and TNFβ. Radiolabeled TNFα and TNFβ (used in various assays for TNF antagonists) was derived as follows. Recombinant human TNFα, in the form of a fusion protein containing a hydrophilic octapeptide at the N-terminus, was expressed in yeast as a secreted protein and purified by affinity chromatography (Hopp et al., *Bio/Technology* 6:1204, 1988). Purified recombinant human TNFIβ was purchased from R&D Systems (Minneapolis, Minn.). Both proteins were radiolabeled to a specific activity of $2 \times 10^{15}$ cpm/mmole using the commercially available solid phase agent, Iodogen (Pierce). In this procedure, 5 µg of Iodogen was plated at the bottom of a 10×75 mm glass tube and incubated for 20 minutes at 4° C. with 75 µl of 0.1M sodium phosphate, pH 7.4 and 20 µl (2 mCi) Na $^{125}$I. This solution was then transferred to a second glass tube containing 5 µg TNFot (or TNFβ) in 45 µl PBS for 20 minutes at 4° C. The reaction mixture was fractionated by gel filtration on a 2 ml bed volume of Sephadex G-25 (Sigma) equilibrated in Roswell Park Memorial Institute (RPMI) 1640 medium containing 2.5% (w/v) bovine serum albumin (BSA), 0.2% (w/v) sodium azide and 20 mM Hepes pH 7.4 (binding medium). The final pool of $^{125}$I-TNF was diluted to a working stock solution of $1 \times 10^{-7}$M in binding medium and stored for up to 3 weeks at 4° C. without significant loss of receptor binding activity.

B. Detection of SFV T2 Binding to TNF Receptors. Two separate binding assays were used to measure T2 protein binding to TNF receptors. In the first method, the presence of SFV T2 in COS-7 cell supernatants was measured by inhibition of $^{125}$I-TNFα binding to U937 cells. Supernatants from COS cells transfected with recombinant SFV T2 ORF constructs were harvested three days post-transfection. Serial two-fold dilutions of this supernatant were pre-incubated with 0.3 nM 125I-TNFα. (specific activity 1×1015 cpm/mmole) for two hours at 4° C. prior to the addition of $2 \times 10^6$ U937 cells. The cells are incubated for an additional two hours at 4° C., after which free and cell bound human $^{125}$I-TNFα were separated using a pthalate oil separation method (Dower et al., *J. Immunol.* 132:751, 1984) essentially as described by Park et al. (*J. Biol. Chem.* 261:4177, 1986). Non-specific ligand binding in all assays was determined by the inclusion of a 200 molar excess of unlabeled ligand.

In the second method, $^{125}$I-TNF binding to T2 protein was detected directly by nitrocellulose dot blots. The ability of TNF receptor or T2 to be stably adsorbed to nitrocellulose from detergent extracts of human cells yet retain binding activity provided a means of detecting T2. Cell extracts were prepared by mixing a cell pellet with a 2× volume of PBS containing 1% Triton X-100 and a cocktail of protease inhibitors (2 mM phenylmethyl sulfonyl fluoride, 10 µM pepslatin, 10 gM leupeptin, 2 mM o-phenanthroline and 2 mM EGTA) by vigorous vortexing. The mixture was incubated on ice for 30 minutes after which it was centrifuged at 12,000×g for 15 minutes at 8° C. to remove nuclei and other debris. Alternatively, recombinant T2 protein in the form of COS supernalants were mixed with an equal volume of PBS/1% Triton X-100 and a cocktail of the same protease inhibitors. Two microliter aliquots of cell extracts or T2 protein extracts were placed on dry BA85/21 nitrocellulose membranes (Schleicher and Schuell, Keene, N.H.) and allowed to dry. The membranes were incubated in tissue culture dishes for 4 hours in Tris (0.05 M) buffered saline (0.15M) pH 7.5 containing 3% w/v BSA to block nonspecific binding sites. The membrane was then covered with $5\times10^{-11}$M $^{125}$I-TNF in PBS+3% BSA and incubated for 2 hr at 4° C. with shaking. At the end of this time, the membranes were washed 3 times in ice-cold PBS, dried and placed on Kodak X-Omat AR film for 18 hr at −70° C.

Example 2

Expression of the SFV T2ORF

A vector (pKTH- 1 ) containing the Shope Fibroma Virus T2 opening reading frame (SFV T2ORF) cloned into pUC19 was obtained from Dr. Grant McFadden of the University of Alberta, Edmonton, Canada. A SpeI/BamHI restriction fragment containing a majority the SFV T2 open reading frame was excised from pKTH-1 by digesting with SpeI and BamlqI restriction enzymes, resulting in a partial SFV T2ORF cDNA fragment from which had been deleted the first 7 codons (including the ATG initiation codon) of the 5' terminus. The 5' terminal coding sequence was reconstructed by ligating to the partial SFV cDNA fragment the following synthetic oligonucleotide, which incorporated a consensus sequence [or optimum translation initiation and contained a 5' terminus compatible with an Asp718 restriction site:

Asp718 SpeI
GTACCGCCACCATGCTTCGTTTAATTGCACTA
(SEQ ID NO: 7)
GCGGTGGTACGAAGCAAATTAACGTGATGATC
(SEQ ID NO: 8)

The resulting cDNA was ligated into the eukaryotic expression vector pDC302 which was digested with the Asp718 and BglII restriction enzymes. pDC302 has been deposited with the American Type Culture Collection, 12301 Parklawn Drive, Rockville, Md. 20842, USA, under the name pCAV/NOT-IL-7R, Accession Number 68014. The resulting expression vector was designated pDC302-SFVT2ORF. pDC302 was assembled from pDC201 (described by Sims et al., *Science* 241:585, 1988 and derived from pMLSV, described by Cosman et al., *Nature* 3 12: 768, 1984), SV40 and cytomegalovirus DNA and comprises, in sequence with the direction of transcription from the origin of replication: (1) SV40 sequences from coordinates 5171-270 including the origin of replication, enhancer sequences and early and late promoters; (2) cytomegalovirus sequences including the promoter and enhancer regions (nucleotides 671 to +63 from the sequence published by Boechart et al. (*Cell* 4 1:521, 1985); (3) adenovirus-2 sequences containing the first exon and part of the intron between the first and second exons of the tripartite leader, the second exon and part of the third exon of the tripartite leader and a multiple cloning site (MCS) containing sites for XhoI, KpnI, Sinai, NotI and BglI; (4) SV40 sequences from coordinates 4127-4100 and 2770-2533 that include the polyadenylation and termination signals for early transcription; (5) sequences derived from pBR322 and virus-associated sequences VAI and VAII of pDC201, with adenovirus sequences 10532–11156 containing the VAI and VAI1 genes, followed by pBR322 sequences from 4363–2486 and 1094–375 containing the ampicillin resistance gene and origin of replication.

SFV T2 protein was then transiently expressed in monkey COS-7 cells as follows. A subconfluent layer COS-7 cells was transfected with pDC302-SFVT2ORF using DEAE-dextran followed by choroquine treatment, as described by Luthman et al., *Nucl. Acids Res.* 11:1295 (1983) and McCutchan et al., *J. Natl. Cancer Inst.* 41:351 (1968). The cells were then grown in culture for three days to permit transient expression of the inserted SFV T2ORF sequences. After three days, cell culture supernatants and the cell monolayers were assayed as described in Example 1, and TNF binding and TNF/TNF receptor binding inhibition was confirmed. COS cells are then bulked up in sufficient quantities to yield several liters of conditioned medium containing microgram quantities of SFV T2 protein.

Example 3

Purification of SFV T2 Protein by TNF Affinity Chromatography

SFV T2 protein is purified from COS cell supernatants of Example 2 using TNF as an affinity ligand. To obtain large amounts of recombinant TNF for preparation of a TNF affinity matrix, a Flag®-TNF fusion protein containing the "Flag®: octapeptide Asp—Tyr— Lys—Asp—Asp—Asp—Asp—Lys fused to the amino terminus of TNF was constructed and expressed. This octapeptide sequence does not alter the biological activity of TNF, is highly antigenic and provides an epitope reversibly bound by a specific monoclonal antibody, enabling facile purification of the expressed TNF (Hopp et al., *Bio/Technology* 6:1204 (1988).

The Flag®-TNF fusion protein is coupled to Affigel-10 (Bio-Rad) or CnBr-activated Sepharose 4B (Pharmacia LKB Biotechnology, Inc.) according to the manufacturer's suggestions and as previously described by Urdal et al., *J. Biol. Chem.* 263:2870 (1988). COS cell conditioned medium from Example 2 is harvested and centrifuged and the resulting conditioned medium (RPMI 1640) is adjusted to 1% BSA, 0.1% sodium azide, 20 mM HEPES, pH 7.4.. To the conditioned medium is added a cocktail of protease inhibitors (2 mM PMSF, 2 mM 0-phenanthroline, 1 mM pepstalin, 1 mM leupeptin). The resulting medium is applied to a Flag®-TNF affinity column equilibrated with PBS, pH 7.4. The column is then washed with 10 column volumes of PBS, pH 7.4, after which bound protein is eluted with 0.1M glycine-HCl, pH 3.0. Eluate containing SFV T2 protein is immediately neutralized with 80 ml of 1.0M HEPES, pH 7.4 and aliquots removed for binding assays (described in Example 1, above) and analysis by SDS-PAGE as previously described by Urdal, *J. Biol. Chem.* 263:2870 (1988).

Example 4

Purification of SFV T2 Protein Usin,, Reversed-Phase HPLC

SFV T2 protein is also purified by conventional methods using Flag®-TNF binding as a biological assay for detection of SFV T2 activity. Flag®-TNF is produced as described in Example 3 above. COS cell conditioned medium from Example 2 is harvested and centrifuged and the resulting conditioned medium (RPMI 1640) is adjuste. d to 1% BSA, 0.1% sodium azide, 0.5M $CaCl_2$ and 20 mM HEPES, pH 7.4.. To the conditioned medium is added a cocktail of protease inhibitors (2 mM PMSF, 2 mM O-phenanthroline, 1 mM pepstalin, 1 mM leupeptin). SFV T2 protein is purified from the resulting medium by conventional purification methods, including ion-exchange, hydrophobic interaction, gel exclusion and reversed-phase HPLC.

Example 5

Preparation of Monoclonal Antibodies to SFV T2 Protein

Preparations of purified recombinant SFV T2, for example, or transfected COS cells expressing high levels of SFV T2 are employed to generate monoclonal antibodies against SFV T2 using conventional techniques, for example, those disclosed in U.S. Pat. No. 4,411,993. Such antibodies are likely to be useful in interfering with TNF binding to TNF receptors, for example, in ameliorating toxic or other undesired effects of TNF, or as components of diagnostic or research assays for TNF or soluble TNF receptor.

To immunize mice, SFV T2 immunogen is emulsified in complete Freund's adjuvant and injected in amounts ranging from 10–100 μg subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS1. Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with SFV T2 or TNF receptor, for example, by adaptations of the techniques disclosed by Engvall et al., *Immunochem.* 8:871 ( 1971) and in U.S. Pat. No. 4,703,004. Positive clones are then injected into the peritoneal cavities of syngeneic Balb/c mice to produce ascites containing high concentrations (>1 m,g/ml) of anti-SFV T2 monoclonal antibody. The resulting monoclonal antibody can be purified by ammonium sulfate precipitation followed by gel exclusion chromatography, and/or affinity chromatography based on binding of antibody to Protein A of *Staphylococcus aureus*.

Example 6

Expression of the Myxoma Virus T2ORF

A vector (pMTN-6) containing the Myxoma Virus T2 opening reading frame (MYXOMA T2ORF) was obtained from Dr. Grant McFadden of the University of Alberta, Edmonton, Canada. This vector was constructed by inserting a Myxoma BamHI fragment (see Russell & Robbins, *Virology* 90: 147) into the BamHI site of pUC19. A NlaIII fragment containing the entire coding region of the MYXOMA T2ORF was isolated from pMyBT-5 and cloned into the SphI site of pMtI21p to create pMTN-6.

The MYXOMA T2ORF was excised from pMTN-6 by digesting with HindlII and PstI restriction enzymes, resulting in a complete MYXOMA T2ORF cDNA fragment. The resulting cDNA was blunt-ended and ligated into the eukaryotic expression vector pDC302 which was digested with the Sinai restriction enzyme. The resulting expression vector was designated pDC302-MVT2ORF-1.

Myxoma T2 protein was then transiently expressed in monkey COS-7 cells as follows. A subconfluent layer COS-7 cells was transfected with pDC302-MVT2ORF using DEAE-dextran followed by choroquine treatment, as described by Luthman et al., *Nucl. Acids Res.* 11:1295 (1983) and McCutchan et al., *J. Natl. Cancer Inst.* 41:351 (1968). The cells were then grown in culture for three days to permit transient expression of the inserted MYXOMA T2ORF sequences. After three days, cell culture supernatants and the cell monolayers are assayed as described in Example 1. The cell culture supernatants did not inhibit binding of TNF to TNF-receptor, possibly because the HindlII/PstI restriction fragment did not contain specific sequences 5' of the coding region which are required for expression. Accordingly, myxoma T2ORF cloned into the mammalian expression vector pDC302 utilizing the polymerase chain reaction (PCR) technique. This method inserts a CACC nucleotide sequence upstream of the initiation codon which is important for optimum initiation of translation (Kozak, *Mol. Cell. Bio.* 8:2737 (1988)). The following primers are used in this construction:

5' End Primer

5'-CCTTGCGGCCGCCACCATGTTTCGTTTAACGCTACTACT-3' (SEQ ID NO: 9)
        NotI site    Initiation Codon 3' End Primer 5'CCTTAGATCTGTAATCTATGAAACGAGTCTACAT-3' (SEQ ID NO: 10)
    BglII site The PCR product thus contains NotI and BglII restriction sites at the 5' and 3' termini, respectively. These restriction sites are used to clone into pDC302. The template for the PCR reaction is the clone myxoma T2 clone, described above, which contains the myxoma T2ORF (pMTN-6). The DNA sequences encoding the myxoma T2ORF (including the upstream Kozak sequences) are then amplified by PCR, substantially as described by Innis et al., eds., *PCR Protocols: A Guide to Methods and Applications* (Academic Press, 1990). The resulting amplified clone is then isolated at ligated into pDC302 and transiently expressed in monkey COS-7 cells as described above. COS cells are then bulked up in sufficient quantities to yield several liters of conditioned medium containing microgram quantities of SFV T2 protein.

Example 7

Purification of Myxoma T2 Protein by TNF Affinity Chromatography

Myxoma T2 protein is purified from COS cell supernatants of Example 6 using TNF as an affinity ligand. To obtain large amounts of recombinant TNF for preparation of a TNF affinity matrix, a Flag®-TNF fusion protein containing the "Flag®" octapeptide Asp—Tyr—Lys—Asp—Asp—Asp—Asp—Lys fused to the amino terminus of TNF was constructed and expressed. This octapeptide sequence does not alter the biological activity of TNF, is highly antigenic and provides an epitope reversibly bound by a specific monoclonal antibody, enabling facile purification of the expressed TNF (Hopp et al., *Bio/Technology* 6:1204 (1988).

The Flag®-TNF fusion protein is coupled to Affigel-10 (Bio-Rad) or CnBr-activated Sepharose 4B (Pharmacia LKB Biotechnology, Inc.) according to the manufacturer's suggestions and as previously described by Urdal et al., *J. Biol. Chem.* 263:2870 (1988). COS cell conditioned medium from Example 6 is harvested and centrifuged and the resulting conditioned medium (RPMI 1640) is adjusted to 1% BSA, 0.1% sodium azide, 20 mM HEPES, pI-t 7.4. To the conditioned medium is added a cocktail of protease inhibitors (2 mM PMSF, 2 mM O-phenanthroline, 1 mM pepstatin, 1 mM leupeptin). The resulting medium is applied to a Flag®-TNF affinity column equilibrated with PBS, pH 7.4. The column is then washed with 10 column volumes of PBS, pH 7.4, after which bound protein is eluted with (). 1M glycine-HCl, pH 3.0. Eluate containing myxoma T2 protein is immediately neutralized with 80 ml of 1.0M HEPES, pH 7.4 and aliquots removed for binding assays (described in Example 1, above) and analysis by SDS-PAGE as previously described by Urdal, *J. Biol. Chem.* 263:2870 (1988).

Example 8

Purification of SFV T2 or Myxoma T2 Protein Using Reversed-Phase HPLC

Myxoma T2 protein is also purified by conventional methods using Flag®-TNF binding as a biological assay for detection of myxoma T2 activity. Flag®-TNF is produced as described in Example 3 above. COS cell conditioned medium from Example 6 is harvested and centrifuged and the resulting conditioned medium (RPMI 1640) is adjusted to 1% BSA, 0.1% sodium azide, (2).5M $CaCl_2$ and 20 mM HEPES, pH 7.4. To the conditioned medium is added a cocktail of protease inhibitors (2 mM PMSF, 2 mM O-phenanthroline, 1 mM pepstatin, 1 mM leupeptin). Myxoma T2 protein is purified from the resulting medium by conventional purification methods, including ion-exchange, hydrophobic interaction, gel exclusion and reversed-phase HPLC.

Example 9

Preparation of Monoclonal Antibodies to Myxoma T2 Protein

Preparations of purified recombinant myxoma T2, for example, or transfected COS cells expressing high levels of myxoma T2 are employed to generate monoclonal antibodies against myxoma T2 using conventional techniques, for example, those disclosed in U.S. Pat. No. 4,411,993. Such antibodies are likely to be useful in interfering with TNF binding to TNF receptors, for example, in ameliorating toxic or other undesired effects of TNF, or as components of diagnostic or research assays for TNF or soluble TNF receptor.

To immunize mice, myxoma T2 immunogen is emulsified in complete Freund's adjuvant and injected in amounts ranging from 10–100 μg subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS1. Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with myxoma T2 or TNF receptor, for example, by adaptations of the techniques disclosed by Engvall et al., *Immunochem.* 8:87 1 ( 1971 ) and in U.S. Pat. No. 4,703,004. Positive clones are then injected into the peritoneal cavities of syngeneic Balb/c mice to produce ascites containing high concentrations (>1 mg/ml) of anti-myxoma T2 monoclonal antibody. The resulting monoclonal antibody can be purified by ammonium sulfate precipitation followed by gel exclusion chromatography, and/or affinity chromatography based on binding of antibody to Protein A of *Staphylococcus aureus.*

Example 10

Expression of the Cowpox virus T2-equivalent (D2) ORF

A full-length CPV T2-equivalent (D2) ORF was isolated from the CPV strain Brighton Red (CPV-BR), and the nucleotide sequence determined by Dr. David Pickup of Duke University, Medical Center, Durham , N.C., U.S.A. (Pickup et al., *Proc. Natl. Acad. Sci. U.S.A.* 83:7698, 1986). The nucleotide sequence was analyzed and determined to be similar to the nucleotide sequences of SFV T2, myxoma T2, and TNFR. The encoded protein was expressed in a vaccinia vital vector in a human osteosarcoma cell line, 143, by Dr. Pickup. Since the CPV T2-equivalent protein was expected to be a secreted protein, supernatant fluid from 143 cells infected with recombinant virus (VV-CPVT2+) and supernatant fluid from 143 cells infected with vector alone (VV) were analyzed for TNF binding activity using two separate binding assays, substantially as described in Example 1, by measuring inhibition of $^{125}$I-TNF binding to U937 cells and by detecting binding of $^{125}$I-TNF to CPV T2-equivalent protein on nitrocellulose dot blots. The results of both assays demonstrated that CPV T2-equivalent protein bound TNF.

Example 11

Purification of CPV T2-equivalent Protein by TNF Affinity Chromatography

CPV T2-equivalent protein is purified from 143 cell supernatants of Example 10 using TNF as an affinity ligand. To obtain large amounts of recombinant TNF for preparation of a TNF affinity matrix, a Flag®-TNF fusion protein containing the "Flag®" octapeptide Asp—Tyr—Lys—Asp—Asp—Asp—Asp—Lys fused to the amino terminus of TNF was constructed and expressed. This octapeptide sequence does not alter the biological activity of TNF, is highly antigenic and provides an epitope reversibly bound by a specific monoclonal antibody, enabling facile purification of the expressed TNF (Hopp et al., *Bio/Technology* 6:1204 (1988).

The Flag®-TNF fusion protein is coupled to Affigel-10 (Bio-Rad) or CnBr-activated Sepharose 4B (Pharmacia LKB Biotechnology, Inc.) according to the manufacturer's suggestions and as previously described by Urdal et al., *J. Biol. Chem.* 263:2870 (1988). 143 cell conditioned medium from Example 10 is harvested and centrifuged and the resulting conditioned medium (RPMI 1640) is adjusted to 1% BSA, 0.1% sodium azide, 20 mM HEPES, pH 7.4.. To the conditioned medium is added a cocktail of protease inhibitors (2 mM PMSF, 2 mM O-phenanthroline, 1 mM pepslatin, 1 mM leupeptin). The resulting medium is applied to a Flag®-TNF affinity column equilibrated with PBS, pit 7.4. The column is then washed with 10 column volumes of PBS, pH 7.4, after which bound protein is eluted with 0.1M glycine-HCl, pH 3.0. Eluate containing CPV T2-equivalent protein is immediately neutralized with 80 ml of 1.0M HEPES, pH 7.4 and aliquots removed for binding assays (described in Example 1, above) and analysis by SDS-PAGE as previously described by Urdal, *J. Biol. Chem.* 263:2870 (1988).

Example 12

Purification of CPV T2-equivalent Protein Using Reversed-Phase HPLC

CPV T2-equivalent protein is also purified by conventional methods using Flag®-TNF binding as a biological assay for detection of CPV T2-equivalent activity. Flag®-TNF is produced as described in Example 3 above. Conditioned medium from Example 10 is harvested and centrifuged and the resulting conditioned medium (RPMI 1640) is adjusted to 1% BSA, 0.1% sodium azide, 0.5M CaCl$_2$ and 20 mM HEPES, pH 7.4. To the conditioned medium is added a cocktail of protease inhibitors (2 mM PMSF, 2 mM O-phenanthroline, 1 mM pepslatin, 1 mM leupeptin). CPV T2-equivalent protein is purified from the resulting medium by conventional purification methods, including ion-exchange, hydrophobic interaction, gel exclusion and reversed-phase HPLC.

Example 13

Preparation of Monoclonal Antibodies to CPV T2-equivalent Protein

Preparations of purified recombinant CPV T2-equivalent, for example, or transfected COS cells expressing high levels of CPV T2-equivalent, are employed to generate monoclonal antibodies against CPV T2-equivalent, using conventional techniques, for example, those disclosed in U.S. Pat. No. 4,411,993. Such antibodies are likely to be useful in interfering with TNF binding to TNF receptors, for example, in ameliorating toxic or other undesired effects of TNF, or as components of diagnostic or research assays for TNF or soluble TNF receptor.

To immunize mice, CPV T2-equivalent immunogen is emulsified in complete Freund's adjuvant and injected in amounts ranging from 10–100 µg subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS 1. Other known myeloma cell lines may be employed in place of NS 1. A preferred murine myeloma cell line is P3×63Ag8.653 (ATCC CRL 1580). Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with 30 CPV T2-equivalent or TNF receptor, for example, by adaptations of the techniques disclosed by Engvall et al., *Immunochem.* 8:871 (1971) and in U.S. Pat. No. 4,703,004. A preferred screening technique is the antibody capture technique described in Beckmann et al. (*J. Immunol.* 144:4212, 1990). Positive clones are then injected into the peritoneal cavities of syngeneic Balb/c mice to produce ascites containing high concentrations (>1 mg/ml) of anti-CPV T2-equivalent monoclonal antibody. The resulting monoclonal antibody can be purified by ammonium sulfate precipitation followed by gel exclusion chromatography, and/or affinity chromatography based on binding of antibody to Protein A of *Staphylococcus aureus*.

We claim:

1. An isolated and substantially homogeneous soluble viral protein selected from the group consisting of Shope fibroma virus T2 protein comprising the sequence of amino acids 1 through 325 of SEQ ID NO: 2, myxoma virus T2 protein comprising the sequence of amino acids 1 through 326 of SEQ ID NO:4, and cowpox virus T2-equivalent protein comprising the sequence of amino acids 1 through 355 of SEQ ID NO:6.

2. An isolated and substantially homogeneous soluble viral protein according to claim 1, comprising the sequence of amino acids 1 through 325 of SEQ ID NO: 2.

3. An isolated and substantially homogeneous soluble vital protein according to claim 1, comprising the sequence of amino acids 1 through 326 of SEQ ID NO:4.

4. An isolated and substantially homogeneous soluble viral protein according to claim 1, comprising the sequence of amino acids 1 through 355 of SEQ ID NO:6.

5. An isolated and substantially homogeneous soluble poxvirus protein which binds TNF and inhibits binding of TNF to a TNF receptor, wherein a DNA encoding the poxvirus protein is selected from the group consisting of SEQ ID NO: 1, nucleotides 192 through 1166; SEQ ID NO: 3, nucleotides 2 through 982; and SEQ ID NO: 5, nucleotides 1 through 1065.

6. An isolated and substantially homogeneous soluble poxvirus protein according to claim 5 selected from the group consisting of poxvirus proteins having inactivated N-linked glycosylation sites, poxvirus proteins having altered protease cleavage sites, poxvirus proteins having altered cysteine residues, poxvirus proteins comprising a peptide added to facilitate purification, and poxvirus proteins containing conservative amino acid substitutions, wherein the soluble poxvirus protein is capable of binding TNF and inhibiting binding of TNF to a TNF receptor.

* * * * *